US009868822B2

(12) United States Patent
Bender et al.

(10) Patent No.: US 9,868,822 B2
(45) Date of Patent: *Jan. 16, 2018

(54) CROSS-LINKED POLYMERS AND MEDICAL PRODUCTS DERIVED FROM NUCLEOPHILICALLY ACTIVATED POLYOXAZOLINE

(71) Applicant: GATT Technologies B.V., Nijmegen (NL)

(72) Inventors: Johannes Caspar Mathias Elizabeth Bender, Overasselt (NL); Richard Hoogenboom, Terneuzen (NL); Jan Cornelis Maria Van Hest, Nijmegen (NL); Harry Van Goor, Heilig Landstichting (NL)

(73) Assignee: GATT Technologies B.V., Nijmegen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/210,606

(22) Filed: Jul. 14, 2016

(65) Prior Publication Data

US 2016/0319075 A1 Nov. 3, 2016

Related U.S. Application Data

(63) Continuation of application No. 14/385,119, filed as application No. PCT/NL2013/050187 on Mar. 15, 2013, now Pat. No. 9,416,228.

(30) Foreign Application Priority Data

Mar. 16, 2012 (EP) ..................... 12159982

(51) Int. Cl.
| | |
|---|---|
| *C08G 69/48* | (2006.01) |
| *C08G 73/02* | (2006.01) |
| *A61L 27/18* | (2006.01) |
| *C08L 79/02* | (2006.01) |
| *A61L 31/10* | (2006.01) |
| *A61L 17/10* | (2006.01) |
| *A61L 24/04* | (2006.01) |
| *A61L 26/00* | (2006.01) |
| *C08J 3/075* | (2006.01) |
| *C08J 3/24* | (2006.01) |

(52) U.S. Cl.
CPC .............. *C08G 69/48* (2013.01); *A61L 17/10* (2013.01); *A61L 24/046* (2013.01); *A61L 26/008* (2013.01); *A61L 26/0019* (2013.01); *A61L 26/0052* (2013.01); *A61L 27/18* (2013.01); *A61L 31/10* (2013.01); *C08G 73/02* (2013.01); *C08G 73/0233* (2013.01); *C08L 79/02* (2013.01); *C08J 3/075* (2013.01); *C08J 3/246* (2013.01); *C08J 2379/02* (2013.01); *C08L 2312/00* (2013.01)

(58) Field of Classification Search
CPC . C08G 73/0233; C08L 79/02; C08L 2203/02; C08L 2312/00; C08L 2666/28; C08L 2666/34; C08L 2666/36; C08L 2666/37; C12N 9/96; C07K 14/47; C07K 14/62; C07K 14/505; C07K 14/535; C07K 7/08; A61K 47/48192; A61K 47/48207
See application file for complete search history.

(56) References Cited

U.S. PATENT DOCUMENTS

| | | | |
|---|---|---|---|
| 3,996,237 A | 12/1976 | Tomalia | |
| 5,635,571 A | 6/1997 | Frechet et al. | |
| 6,566,406 B1 | 5/2003 | Pathak et al. | |
| 9,416,228 B2 * | 8/2016 | Bender | ................... A61L 27/18 |
| 2002/0042473 A1 | 4/2002 | Trollsas et al. | |
| 2003/0119985 A1 | 6/2003 | Sehl et al. | |

(Continued)

FOREIGN PATENT DOCUMENTS

| | | |
|---|---|---|
| GB | 0 760 311 A | 10/1956 |
| GB | 1 164 582 A | 9/1969 |

(Continued)

OTHER PUBLICATIONS

Bentolila, A. et al., "Poly(N-acryl amino acids): A new class of biologically active polyanions", Journal of Medicinval Chemistry, American Chemical Society, vol. 43, Jan. 1, 2000, pp. 2591-2600.
Cesana et al., "First poly(2-oxazoline)s with pendant amino groups," Macromolecular Chemistry and Physics, 2006, vol. 207, pp. 182-192.
Chujo, et al. "Reversible Gelation of Polyoxazoline by Means of Diels-alder Reaction", Macromolecules, 1990, vol. 23, pp. 2636-2641.
Diehl Christina et al, "Thermo-responsive polyoxazolines with widely tuneable LCSTa", Database Medline, US National Library of Medicine, Feb. 2009, vol. 9, No. 2, pp. 157-161.
Inata, H. et al., "Postcrosslinking of linear polyesters. II. UV-induced crosslinking agents having carboxyl reactive group", Journal of Applied Polymer Science, vol. 36, No. 7, 1988, pp. 1667-1672.
International Search Report in PCT/NL2012/050001 dated May 16, 2012.

(Continued)

Primary Examiner — Robert Jones, Jr.
(74) Attorney, Agent, or Firm — Gilberto M. Villacorta; Sunit Talapatra; Foley & Lardner LLP

(57) ABSTRACT

One aspect of the invention relates to a biocompatible medical product comprising at least 1% by weight of dry matter of a covalently cross-linked polymer that is obtained by reacting a nucleophilically activated polyoxazoline (NU-PDX) with an electrophilic cross-linking agent other than an electrophilically activated polyoxazoline, said NU-PDX comprising m nucleophilic groups; and said electrophilic cross-linking agent comprising n electrophilic groups, wherein the m nucleophilic groups are capable of reaction with the n electrophilic groups to form covalent bonds; wherein m≥2, n≥2 and m+n≥5; and wherein the NU-PDX comprises at least 30 oxazoline units in case the electrophilic cross-linking agent is an isocyanate.
Also provided is a kit for producing the aforementioned biocompatible cross-linked polymer.
The biocompatible cross-linked polymers according to the invention have excellent implant and/or sealing characteristics.

23 Claims, No Drawings

(56) References Cited

U.S. PATENT DOCUMENTS

| | | |
|---|---|---|
| 2004/0157157 A1 | 8/2004 | Saito et al. |
| 2005/0002893 A1 | 1/2005 | Goldmann |
| 2011/0123453 A1 | 5/2011 | Bentley et al. |
| 2012/0041481 A1 | 2/2012 | Daniloff et al. |

FOREIGN PATENT DOCUMENTS

| | | |
|---|---|---|
| JP | 2005-161698 A | 6/2005 |
| WO | WO-00/33764 A1 | 6/2000 |
| WO | WO-00/71600 A1 | 11/2000 |
| WO | WO-02/062276 | 8/2002 |
| WO | WO-02/102864 A1 | 12/2002 |
| WO | WO-2005/109248 | 11/2005 |
| WO | WO-2006/034128 A2 | 3/2006 |
| WO | WO-2006/078282 A2 | 7/2006 |
| WO | WO-2009/043027 A2 | 4/2009 |
| WO | WO-2009/089542 A2 | 7/2009 |
| WO | WO-2009/112402 A1 | 9/2009 |
| WO | WO-2010/033207 A1 | 3/2010 |
| WO | WO-2010/043979 A2 | 4/2010 |
| WO | WO-2010/059280 | 5/2010 |
| WO | WO-2012/057628 A2 | 5/2012 |

OTHER PUBLICATIONS

International Search Report in PCT/NL2012/050933 dated May 7, 2013.
International Search Report of PCT/NL2013/050187 dated Apr. 25, 2013.
Liu, et al. "Shell Cross-Linked Micelle-Based Nanoreactors for the Substrate-Selective Hydrolytic Kinetic Resolution of Epoxides", J. Am. Chem. Soc., (2011), vol. 133, 1426001314263.
Luxenhofer, et al. "Novel Functional Poly(2-oxazoline)s as Potential Carriers for Biomedical Applications. Dissertation", Internet Citation, 2007, XP008138013, http://mediatum2.ub.tum.de/doc/620620/document.pdf. (Table of Contents).
Mero, et al. "Synthesis and characterization of poly(2-ethyl2-oxazoline)-conjugates with proteins and drugs: Suitable alternatives to PEG-conjugates?", Journal of Controlled Release, Oct. 2007, vol. 125, No. 2, pp. 87-95.
Richter, R. et al., "Uber die Umsetzungen von 2-alkyl-Delta2-oxazolinen and 2-methyl-Delta2-thiazolin mit Arylisocyanaten", Liebigs Ann. Chem., vol. 743, 1971, pp. 10-24.
Santini, et al. "Synthesis and Bulk Assembly Behavior of Linear-Dendritic Rod Diblock Copolymers", Journal of Polymer Science: Part A: Polymer Chemistry, (2004), vol. 42, pp. 2784-2814.
Zarka, et al. "Amphiphilic Polymer Supports for the Asymmetric Hydrogenation of Amino Acid Precursors in Water", Chem. Eur. J. (2003), vol. 9, pp. 3228-3234.

* cited by examiner

CROSS-LINKED POLYMERS AND MEDICAL PRODUCTS DERIVED FROM NUCLEOPHILICALLY ACTIVATED POLYOXAZOLINE

CROSS-REFERENCE TO RELATED APPLICATIONS

The present application is a Continuation application of U.S. application Ser. No. 14/385,119, filed Sep. 12, 2014, which is the U.S. National Stage of International Application No. PCT/NL2013/050187 filed on Mar. 15, 2013, published as WO 2013/137736, and which claims the benefit of European Application. No. 12159982.3 filed Mar. 16, 2012, the entire disclosures of which are incorporated herein by reference.

TECHNICAL FIELD OF THE INVENTION

The invention relates to a biocompatible, covalently cross-linked polymer that is obtained by reacting nucleophilically activated polyoxazoline (NU-POX) with an electrophilically activated cross-linking agent.

Also provided is a kit for producing a biocompatible, cross-linked polymer from NU-POX with an electrophilically activated cross-linking agent.

The invention further provides a medical product comprising at least 1% by weight of dry matter of said cross-linked polymer. Examples of such medical products are medical implants including bone implants, soft tissue implants, adhesive implants, coatings on implants, sutures, adhesive tissue sealants and adhesive tissue tapes.

BACKGROUND OF THE INVENTION

Tissue adhesives have many potential medical applications, including wound closure, supplementing or replacing sutures or staples in surgical procedures, adhesion of synthetic onlays or inlays to the cornea, drug delivery devices, and as anti-adhesion barriers to prevent post-surgical adhesions.

Conventional tissue adhesives include fibrin sealants, cyanoacrylate based sealants, and other synthetic sealants and polymerizable macromers. Some of these conventional sealants are only suitable for a specific range of adhesive applications. For example, cyanoacrylate-based adhesives have been used for topical wound closure, but the release of toxic degradation products limits their use for internal applications. Fibrin-based adhesives are expensive, often need refrigerated storage, are slow curing, have limited mechanical strength, and pose a risk of viral infection.

For certain applications, for example, ophthalmic applications such as sealing wounds resulting from trauma such as corneal lacerations, or from surgical procedures such as vitrectomy procedures, abdominal hernias, cataract surgery, LASIK surgery, glaucoma surgery, and corneal transplants; neurosurgery applications, such as sealing the dura; plugging to seal a fistula or the punctum, slow degrading tissue adhesives are needed.

The last decade, several types of (semi)synthetic hydrogel tissue adhesives have been developed, which have improved adhesive properties and are non-toxic. Most of these hydrogel tissue adhesives, like DuraSeal®, are chemically based on a process called PEGylation used in polymer-modified therapeutics with reactive polyethylene glycol (PEG) precursors like, for instance, PEG-succinimidyl glutarate. These hydrogel tissue adhesives, based on PEGylation, typically swell or dissolve away too quickly, or lack sufficient cohesion (interconnecting mechanical strength), thereby decreasing their effectiveness as surgical adhesives. Moreover, to apply these hydrogel tissue adhesives, dual syringe spray technology may be needed, which demands extensive sample preparation from freeze dried starting materials. Finally, the properties of such PEG-based materials cannot be easily controlled and the number of NHS-groups is limited to the number of chain ends; possibly comprising multiple NHS groups per chain end resulting in a high NHS group density rather than regularly distributed groups.

WO 2002/062276 describes a hydrogel tissue sealant comprising a star-shaped PEG-succinimidyl glutarate precursor, also known as star-PEG-NHS or star-PEG-NS or star-SG-PEG or star-PEG-SG, that reacts with a trilysine precursor. The star-SG-PEG precursor may be reconstituted in pH 4 phosphate, while the trilysine precursor may be reconstituted in pH 8 borate buffer. Upon mixing, covalent amide bonds between amines of the trilysine precursor and NHS-activated terminal carboxylate groups of the star-SG-PEG precursor are formed.

WO 2010/059280 describes an anhydrous fibrous sheet comprising a first component of fibrous polymer, said polymer containing electrophilic groups or nucleophilic groups, and a second component capable of crosslinking the first component when said sheet is exposed to an aqueous medium to form a crosslinked hydrogel that is adhesive to biological tissue. The examples of the international patent application describe the preparation of fibrous sheets comprising dextran aldehyde and multi-arm polyethylene glycol amine.

WO 00/33764 describes a method for preparing a biocompatible crosslinked polymer, comprising:
  providing a biocompatible small molecule crosslinker having n crosslinker functional groups, wherein n is two or more, and wherein the crosslinker functional groups are either electrophilic or nucleophilic;
  dissolving the biocompatible small molecule crosslinker in a first solvent to form a crosslinker solution;
  providing a biocompatible functional polymer having m functional polymer functional groups, wherein m is two or more and the sum of n and m is five or more, and wherein the functional polymer functional groups are nucleophilic if the crosslinker functional groups are electrophilic, and the functional polymer functional groups are electrophilic if the crosslinker functional groups are nucleophilic;
  dissolving the biocompatible functional polymer in a second solvent to form a functional polymer solution; and
  combining the crosslinker and functional polymer solutions to react the crosslinker functional groups with the functional polymer functional groups.

Polyoxazoline is nowhere mentioned in WO 00/33764.

WO 2005/109248 describes cross-linked polymeric compositions of hydrolyzed poly (2-alkyl-2-oxazoline) and the use of these cross-linked polymeric compositions in color ink-jet ink.

WO 2009/043027 describes multiarmed, monofunctional derivatives of polyoxazolines, as well as conjugates of such polyoxaline derivatives with drugs.

Preparation of a cross-linked, polymer by reacting nucleophilically activated polyoxazoline (NU-POX) with an electrophilically activated cross-linking agent has been described by Luxenhofer (Thesis: *Novel Functional Poly(2-*

*oxazoline)s as Potential Carriers for Biomedical Applications*, Technische Universitat München (2007)). A poly(2-oxazoline) comprising 20 units of 2-methyl-2-oxazoline and 5 units of 2-aminoethyl-2-oxazoline was cross-linked with hexamethylene diisocyanate. Due to the high reactivity of isocyanates towards water, the hydrogel preparation had to be performed in the absence of water. As a good and water compatible (for subsequent swelling) solvent for poly(2-oxazoline)s acetonitrile was chosen. The cross-linker was directly added to the solvent which was subsequently added to the lyophylized polymer. After 10 min 1.5 mL of water was added upon which the hydrogel immediately swelled.

Chujo et al. (*Reversible Gelation of Polyoxazoline by Means of Diels-Alder Reaction*, Macromolecules, 1990(23), 2636-2641) describes the preparation of a polyoxazoline hydrogel by means of intermolecular Diels-Alder reaction between furan-modified poly(N-acetylethylenimine) (PAEI) and maleimide-modified PAEI, which were synthesized from the partially hydrolyzed PAEIs by the reaction with furan- or maleimidecarboxylic acid, respectively, in the presence of dicyclohexylcarbodiimide.

It is of interest to expand the range of polymers having implant or tissue sealant applications, especially to provide polymers having properties not possessed by PEG-based polymers while being similarly biocompatible.

SUMMARY OF THE INVENTION

The inventors have discovered that a polymer having excellent implant and/or sealing characteristics can be obtained by reacting a nucleophilically activated polyoxazoline (NU-POX) and at least two nucleophilic groups with a cross-linking agent that comprises at least two electrophilic groups, said cross-linking agent not being an electrophilically activated polyoxazoline.

Thus, the invention provides a biocompatible medical product comprising a covalently cross-linked, polymer that is obtained by reacting a NU-POX with an electrophilic cross-linking agent other than an electrophilically activated polyoxazoline, said NU-POX comprising m nucleophilic groups; and said electrophilic cross-linking agent comprising n electrophilic groups, wherein the m nucleophilic groups are capable of reaction with the n electrophilic groups to form covalent bonds; wherein m≥2, n≥2 and m+n≥5, and wherein the NU-POX comprises at least 30 oxazoline units in case the electrophilic cross-linking agent is an isocyanate.

Examples of biocompatible medical products according to the present invention include implants, tissue sealants, adhesive tissue tape, suture materials, polymer coated stents and haemostatic materials.

The cross-linked polymer of the present invention provides a number of beneficial properties:

Mechanical properties of the cross-linked polymer can be manipulated effectively by controlling the level and nature of alkyl side chain and/or end-group functionalization and the polymer chain length. Cationic 2-oxazoline polymerization can suitably be used to incorporate a large number of activated groups in the alkyl side chains of the POX polymer;

Adhesive properties of the cross-linked polymer can be varied by using different electrophilic cross-linking agents and by varying the amount of electrophilic cross-linking agent that is used in the preparation of the cross-linked polymer.

Cohesiveness of the cross-linked polymer is determined largely by the number/density of cross-links within the polymer. The number of cross-links in the polymer can be varied within wide ranges by incorporating different amounts of activated groups in the side chains of the POX;

The swelling index of the cross-linked polymer can be controlled by manipulating the number of cross-links and the size of the side chains in the POX;

Implants made of the cross-linked polymer are an ideal drug depot for local drug delivery. The release of drugs, such as antibiotics, growth factors like VEGF and osteogenic factor (BMP-2), may be sustained by slow diffusion from the interconnecting network depending on the nature of the alkyl side chains and the density of cross links within the network and the degradability;

Biodegradability of the cross-linked polymer can be controlled effectively by incorporating hydrolysable groups, such as esters or carbonates, into the copolymers. It is further influenced by the number of internal cross links. Thus, it is possible to fine tune the biodegradability of the polymer to the intended use;

Based on end capped POX-NHS in research for drug delivery, POX seems to have similar or even better stealth and antifouling behaviour than PEG. For renal clearance the POX should preferably have a Mw of 30,000 or less.

Another aspect of the invention relates to a biocompatible, covalently cross-linked polymer that is obtained by reacting NU-POX with an electrophilic cross-linking agent other than an electrophilically activated polyoxazoline, said NU-POX comprising m nucleophilic groups; and said electrophilic cross-linking agent comprising n electrophilic groups, wherein the m nucleophilic groups are capable of reaction with the electrophilic groups to form covalent bonds; wherein m≥2, n≥2 and m+n≥5; wherein the NU-POX comprises at least 30 oxazoline units in case the electrophilic cross-linking agent is an isocyanate; and wherein the total number of reacted and unreacted electrophilic groups contained in the polymer exceeds the total number of reacted and unreacted nucleophilic groups contained in the polymer by at least 3%, preferably at least 5%.

Yet another aspect of the invention relates to a kit for producing a biocompatible, cross-linked polymer, said kit comprising the NU-POX and the electrophilically activated cross-linking agent described herein before. This kit may suitably be used to deliver bone substitute materials, anti-adhesive implants (films), adhesive implants (for instance a tissue sealant for closing arterial puncture sites, or for embolization or to treat urinary incontinence).

The rate at which cross-linking occurs when the NU-POX and the electrophilically activated cross-linking agent are brought together can be controlled effectively by including non-inert fluids, such as water (various pH), alcohols and/or polyols.

The NU-POX component of the biocompatible medical product of the present invention offers the following advantages:

Due to its hydrophilic/hydrophobic balance, NU-POX can be soluble in organic fluids like ethanol and dichloromethane as well as in water.

NU-POX has excellent amorphous properties with a glass transition temperature markedly higher compared to, for instance, polyethylene glycol.

NU-POX has film forming capabilities and is easy to plasticize with limited amounts of plasticizers.

An advantage of NU-POX over nucleophilically activated PEG is the possibility to incorporate different and also functionalized groups along the chain in order to tune the polymer properties for specific applications;

Another advantage of NU-POX over nucleophilically activated PEG is that NU-POX may be co-polymerized, allowing the preparation of a cross-linked copolymer with mechanical characteristics that can vary within a wide range;

NU-POX provides a protective environment for electrophilic groups in the implant when it is not exposed to water or bodily fluids.

DETAILED DESCRIPTION OF THE INVENTION

Accordingly, one aspect of the invention relates to a biocompatible medical product comprising at least 1% by weight of dry matter of covalently cross-linked polymer that is obtained by reacting a nucleophilically activated polyoxazoline (NU-POX) with an electrophilically activated cross-linking agent other than an electrophilically activated polyoxazoline, said NU-POX comprising m nucleophilic groups, and said electrophilically activated cross-linking agent comprising n electrophilic groups, wherein the m nucleophilic groups are capable of reaction with the n electrophilic groups to form covalent bonds, wherein m≥2, n≥2 and m+n≥5, wherein the NU-POX comprises at least 30 oxazoline units in case the electrophilic cross-linking agent is an isocyanate.

The term "polyoxazoline" as used herein refers to a poly(N-acylalkylenimine) or a poly(aroylalkylenimine) and is further referred to as POX. The term "polyoxazoline" as used herein also encompasses POX copolymers.

The terminology "electrophilically activated cross-linking agent" as used herein refers to a polyoxazoline containing at least 2 electrophilic groups, notably electrophilic groups selected from electrophilic groups contained in the EL-POX are selected from carboxylic acid esters, sulfonate esters, phosphonate esters, thioesters, pentafluorophenyl esters, p-nitrophenyl esters, p-nitrothiophenyl esters, acid halide groups, anhydrides, ketones, aldehydes, isocyanato, thioisocyanato, isocyano, epoxides, activated hydroxyl groups, olefins, glycidyl ethers, carboxyl, succinimidyl ester, succinimidyl carbonate, succinimidyl carbamates, sulfosuccinimidyl ester, sulfosuccinimidyl carbonate, maleimido (maleimidyl), ethenesulfonyl, imido esters, aceto acetate, halo acetal, orthopyridyl disulfide, dihydroxy-phenyl derivatives, vinyl, acrylate, acrylamide, iodoacetamide and combinations thereof.

The terminology "pendant nucleophilic group" refers to a nucleophilic group that is comprised in a side chain, e.g. an alkyl or aryl side chain, of the POX polymer, as opposed to a nucleophilic group that is located at a terminus of the POX polymer chain.

It should be understood that a particular side chain of the POX polymer may suitably contain more than one nucleophilic group, in which case each nucleophilic group within that particular side chain counts as a pendant nucleophilic group.

The term "amine groups" as used herein refers to primary or secondary amine groups.

Whenever the NU-POX or the cross-linked polymer of the present invention is characterized on the basis of the presence of a certain number of particular groups or bonds per 100 monomers it should be understood that this does not imply that the polymer contains at least 100 monomers. For example, a NU-POX comprising 80 monomers and 8 pendant groups contains 10 pendant groups per 100 monomers. Likewise, if a NU-POX contains 80 monomers and it is specified that this polymer contains, for instance, at least x pendant groups per 100 monomers, this criterion is met if this particular polymer contains on average at least 0.8x pendant groups.

The NU-POX of the present invention is a nucleophilically activated version of a polyoxazoline polymer whose repeating units are represented by the following formula (I):

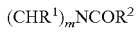

$(CHR^1)_m NCOR^2$ $R^2$, and each of $R^1$ independently being selected from H, optionally substituted $C_{1-22}$ alkyl, optionally substituted cycloalkyl, optionally substituted aralkyl, optionally substituted aryl; and m being 2 or 3. The invention also encompasses the use of polyoxazolines copolymers that comprise two or more different repeating units that are represented by formula (I).

Preferably, $R^1$ and $R^2$ in formula (I) are selected from H and $C_{1-22}$ alkyl, even more preferably from H and $C_{1-4}$ alkyl. $R^1$ most preferably is H. The integer m in formula (I) is preferably equal to 2.

In a preferred embodiment, the polyoxazoline employed in accordance with the present invention is a polymer, more preferably a homopolymer, of 2-alkyl-2-oxazoline, said 2-alkyl-2-oxazoline being selected from 2-methyl-2-oxazoline, 2-ethyl-2-oxazoline, 2-propyl-2-oxazoline, and combinations thereof. Even more preferably, the 2-alkyl-oxazoline is selected from 2-methyl-2-oxazoline, 2-ethyl-2-oxazoline and combinations thereof. Most preferably, the 2-alkyl-2-oxazoline is 2-methyl-oxazoline.

In case the electrophilic cross-linking agent is an isocyanate, the NU-POX employed in accordance with the present invention advantageously contains at least 40, even more preferably at least 50 and most preferably at least 100 (monomeric) oxazoline units.

According to a particularly preferred embodiment at least one of the two reactants employed in the cross-linked polymer of the present invention, i.e. the NU-POX and/or the electrophilic cross-linking agent, is a polymer having a degree of polymerization of at least 20, more preferably at least 30, even more preferably of least 50 and most preferably of at least 100.

The use of a NU-POX having a high degree of polymerization enables the preparation of resilient cross-linked polymers that are ideally suited for application in tissue sealants, implants etc. Accordingly, in a preferred embodiment, the NU-POX contains at least 20, even more preferably at least 30, yet more preferably at least 50 and most preferably at least 100 (monomeric) oxazoline units The NU-POX employed in accordance with the present invention contains pendant nucleophilic groups, terminal nucleophilic groups, or a combination thereof. Preferably, at least one of the m nucleophilic groups in the NU-POX being part of the biocompatible cross-linked polymer according to any of the foregoing is a pendant nucleophilic group. Typically, said NU-POX contains 3 to 50 pendant nucleophilic groups per 100 monomers in the cross-linked polymer, more preferably 5 to 20 pendant electrophilic groups per 100 monomers in the cross-linked polymer.

According to a particularly preferred embodiment of the invention, the cross-linked polymer has tissue-adhesive properties. Whenever the terminology "tissue adhesive" is used herein in relation to the cross-linked polymer, it means that the unreacted electrophilic groups contained in the cross-linked polymer are capable of reacting with nucleophilic (e.g. amine or thiol) groups that are naturally present in tissue to form covalent bonds. Preferably, the total number of reacted and unreacted electrophilic groups contained in the polymer exceeds the total number of reacted and unreacted nucleophilic groups contained in the polymer by at least 3%, preferably by at least 5%, even more preferably by at least 10% and most preferably by at least 20%.

The tissue adhesive properties of the cross-linked polymer can be controlled very effectively by manipulating the number of non-reacted electrophilic groups in the cross-linked polymer. Generally speaking, the higher the number of non-reacted electrophilic groups, the stronger the adhesion. Preferably, the cross-linked polymer comprises, per 100 NU-POX monomers, at least 2, more preferably at least 5 and most preferably at least 10 electrophilic groups of the electrophilic cross-linking agent that have not reacted with a nucleophilic group of the NU-POX.

Preferably, the m nucleophilic groups on NU-POX are selected from amine groups, thiol groups, phosphine groups and combination thereof. Even more preferably, the nucleophilic groups are selected from amine groups, thiol groups and combinations thereof.

According to one preferred embodiment, the nucleophilic groups present in the NU-POX are amine groups. An amine functionalized NU-POX can suitably be derived from a homopolymer or copolymer of cysteamine modified 2-alkenyl-2-oxazoline or 2-t-BOC-aminoalkyl-2-oxazoline and 2-alkyl-2-oxazoline. The cysteamine modified 2-alkenyl-2-oxazoline comprised in the copolymer is preferably selected from 2-butenyl-2-oxazoline, and combinations thereof. The 2-alkyl-2-oxazoline is preferably selected from 2-ethyl-2-oxazoline, 2-methyl-2-oxazoline, 2-propyl-2-oxazoline and combinations thereof. The amine moieties can also be introduced by partial hydrolysis of POX followed by alkylation or amidation of the resulting secondary amine groups in the polymer chain.

According to another preferred embodiment, the m nucleophilic groups present in the NU-POX are thiol (sulfohydryl) groups. Even more preferably, the NU-POX is a poly(2-alkyl-2-oxazoline) with thiol terminal groups that have been introduced by endcapping the polymerization with a multifunctional initiator with potassium xanthogenate followed by aminolysis to get the free thiol groups. Alternatively, the thiol moieties are introduced into the side chains of the NU-POX by copolymerization of a protected thiol containing monomer or by modification of acid, amine or alkenyl side chains or by modification of the backbone secondary amines resulting from partial hydrolysis. The 2-alkyl-2-oxazoline is preferably selected from 2-ethyl-2-oxazoline, 2-methyl-2-oxazoline, 2-propyl-2-oxazoline and combinations thereof.

According to a preferred embodiment, the NU-POX contains oxazoline units containing a nucleophilic group and oxazoline units containing no nucleophilic group in a molar ratio that lies within the range of 1:50 to 1:1, more preferably in a molar ratio that lies within the range of 3:100 to 1:2.

The NU-POX employed in accordance with the present invention typically has a molecular weight in the range of 1,000 to 100,000 g/mol, more preferably of 5,000 to 50,000 and most preferably of 10,000 to 30,000 g/mol.

The NU-POX employed in accordance with the present invention can be a homopolymer or a copolymer. Most preferably, NU-POX is a copolymer.

The electrophilically activated cross-linking agent employed in accordance with the present invention contains a backbone that carries or is substituted with n≥2 electrophilic groups. The backbone preferably is chosen from the group consisting of polymers, diacids, triacids or higher acids. The backbone of the electrophilically activated cross-linking agent is not a polyoxazoline.

In a preferred embodiment the backbone of the electrophilically activated cross-linking agent is selected from the group of polymers consisting of polyesters, polyolefins, polystyrenes, polycarbonates, polyamides, polyacetates, poly(alkylene oxalates), polyanhydrides, poly iminocarbonates, polyoxaesters, polyorthoesters, polyphosphazenes, polyphosphoesters, polyethers, polyetheresters, polyacrylamides, polyimides, polyphenylenes, polysilanes, polysiloxanes, polybenzimidazoles, polybenzothiazoles, polysulfides, polyesteramides, polyetheramides, polyamines, polyetheramines, polyarylene vinylenes, polyether ketones, polyurethanes, polysulfones, polyacrylates, polymethacrylates, polysaccharides, glycosaminoglycans, polypeptides, and combinations thereof. Typically, these polymers have a molecular weight in the range of 1,000-100,000.

Even more preferably, the backbone of the electrophilically activated cross-linking agent is selected from the group of polymers consisting of agar, starch, pullulan, inulin, levan, silk, fibronectin, pectin, cellulose (e.g. carboxymethyl cellulose, hydroxyethyl cellulose, oxidized cellulose or methyl cellulose), collagen, elastin, gelatin, albumin, fibrin, fibrinogen, dextran, methyl cellulose, hyaluronic acid, chondroitin sulfate, keratosulfate, heparan sulfate, dermatan sulfate, alginic acid, chitosan, chitin, heparin, polyvinyl alcohol, polyethylene glycol and combinations thereof. The backbone of the electrophilically activated cross-linking agent may suitably be selected from the group of polysaccharides consisting of dextran (e.g. carboxymethyldextran), starch, agar, cellulose pullulan, inulin, levan, and hyaluronic acid. In accordance with a particularly advantageous embodiment, the latter polysaccharides are employed in a (partially) oxidized form.

Most preferably, the electrophilic cross-linking agent is selected from the group of polymers consisting of dextran, collagen, gelatin (gelfoam), alginic acid and polyethylene glycol.

In another preferred embodiment the electrophilic cross-linking agent employed in the biocompatible cross-linked polymer is a low molecular weight electrophilic cross-linker having a molecular weight of 80-1000 g/mol, preferably of 100-500 g/mol. Examples of low molecular cross-linking agents that may suitably be employed include multialdehydes, multimaleimides, multi-activated esters and combinations thereof (here the term 'multi' means at least two). According to a preferred embodiment, the low-molecular cross-linker has a backbone consisting of an acid selected from the group consisting of diacids, triacids and higher acids modified with N-hydroxysuccinimide (NHS) or sulfo-NHS. Even more preferably, the acid-based cross-linking agent is selected from diacids, triacids and combinations thereof. Non-limiting examples of diacids and triacids that may be employed are diglycolic acid, oxalic acids, malonic acids, malic acid, tartaric acid, maleic acid, succinic acid, glutaric acid, adipic acid, pimelic acid, suberic acid, azelaic acid, sebacic acid, phthalic acid, tetrahydrophthalic acid, hexahydrophthalic acid, trimesic acid, mellitic acid, isophthalic acid, terephthalic acid, citric acid, isocitric acid, aconitic acid, tricarballylic acid and trimesic acid. Most preferably, the acid that forms the backbone of the electrophilic cross-linking agent is selected from triacids, most preferably citric acid.

Preferably, the acid-based cross-linking agent is selected from the group of amino carboxylic acids. Non-limiting examples of amino carboxylic acids that may be employed are: Fura-2, iminodiacetic acid, nitrilotriacetic acid, ethylenediaminetetraacetic acid, diethylene triamine pentaacetic acid, ethylene glycol tetraacetic acid, (1,2-bis(o-aminophenoxy)ethane-N,N,N,N-tetraacetic acid), 1,4,7,10-tetraazacyclododecane-1,4,7,10-tetraacetic acid and oligopeptides based on glutamic acid and/or aspartic acid.

According to a particularly preferred embodiment, the electrophilic cross-linking agent is a polymer having a molecular weight in excess of 1000 g/mol, more preferably of 2000-10000 g/mol and most preferably of 5000-50000 g/mol. The use of polymeric electrophilic cross-linking agents offers the advantage that the excess electrophilic groups are further away from the crosslinking points thereby increasing their mobility and ability to couple to tissue.

The electrophilic groups contained in the cross-linking agent preferably are highly reactive towards the nucleophilic groups contained in the NU-POX, preferably at ambient and/or physiological conditions.

The electrophilic groups present in the cross-linking agent are preferably selected from carboxylic acid esters, sulfonate esters, phosphonate esters, thioesters, pentafluorophenyl esters, p-nitrophenyl esters, p-nitrothiophenyl esters, acid halide groups, anhydrides, ketones, aldehydes, isocyanato, thioisocyanato (isothiocyanato), epoxides, activated hydroxyl groups, glycidyl ethers, carboxyl, succinimidyl esters, succinimidyl carbonates, succinimidyl carbamates, sulfosuccinimidyl esters, sulfosuccinimidyl carbonates, maleimides, imido esters, orthopyridyl disulfide, dihydroxyphenyl derivatives, vinyl, acrylate, acrylamide, iodoacetamide, halo acetals, orthopyridyl disulfide, vinyl sulfone, dihydroxyphenyl derivatives, iodoacetamide, and combinations thereof.

Examples of sulfonate esters that can be used as electrophilic groups include mesylate, tosylate, nosylate, triflate and combinations thereof. Examples of activated hydroxyl groups include hydroxyl groups that have been activated with an activating agent selected from p-nitrophenyl chlorocarbonates, carbonyldiimidazoles (e.g. 1,1-carbonyl diimidazole) and sulfonyl chloride.

Examples of succinimidyl derivatives that may be employed include succinimidyl glutarate, succinimidyl propionate, succinimidyl succinamide, succinimidyl carbonate, disuccinimidyl suberate, bis(sulfosuccinimidyl) suberate, dithiobis(succinimidylpropionate), bis(2-succinimidooxycarbonyloxy) ethyl sulfone and 3,3'-dithiobis(sulfosuccinimidyl-propionate). Examples of sulfosuccinimidyl derivatives that can be used include sulfosuccinimidyl(4-iodoacetyl)aminobenzoate, bis(sulfosuccinimidyl) suberate, sulfosuccinimidyl-4-(N-maleimidomethyl)-cyclohexane-1-carboxylate, dithiobis-sulfosuccinimidyl propionate, disulfo-succinimidyl tartarate; bis[2-(sulfo-succinimidyloxycarbonyloxy ethylsulfone)], ethylene glycol bis(sulfosuccinimiclylsuccinate), dithiobis-(succinimidyl propionate). Examples of dihydroxyphenyl derivatives include dihydroxyphenylalanine, 3,4-dihydroxyphenylalanine (DOPA), dopamine, 3,4-dihydroxyhydroccinamic acid (DOHA), norepinephrine, epinephrine and catechol.

According to one preferred embodiment, the m≥2 nucleophilic groups of the NU-POX are amine groups, preferably primary amine groups, and the n≥2 electrophilic groups comprised in the electrophilically activated cross-linking agent are selected from carboxylic acid esters, sulfonate esters, phosphonate esters, thioesters, pentafluorophenyl esters, p-nitrophenyl esters, p-nitrothiophenyl esters, acid halide groups, anhydrides, ketones, aldehydes, isocyanato, thioisocyanato, epoxides, activated hydroxyl groups, glycidyl ethers, carboxyl, succinimidyl esters, succinimidyl carbonates, succinimidyl carbamates, sulfosuccinimidyl esters, sulfosuccinimidyl carbonates, imido esters, dihydroxy-phenyl derivatives, and combinations thereof. Even more preferably, the electrophilic groups contained in the cross-linking agent are selected from aldehydes, succinimidyl esters, succinimidyl carbonates, succinimidyl carbamates, imido esters, dihydroxyphenyl derivatives and combinations thereof. Most preferably, the electrophilic groups are selected from the group of N-hydroxysuccinimide esters, aldehydes, dihydroxyphenyl derivatives and combinations thereof.

According to another preferred embodiment, the m≥2 nucleophilic groups of the NU-POX are thiol groups and the n≥2 electrophilic groups contained in the electrophilically activated cross-linking agent are selected from halo acetals, orthopyridyl disulfide, maleimides, vinyl sulfone, dihydroxyphenyl derivatives, vinyl, acrylate, acrylamide, iodoacetamide, succinimidyl esters, succinimidyl carbonate, succinimidyl carbamates, sulfosuccinimidyl esters, sulfosuccinimidyl carbonates and combinations thereof. More preferably, the electrophilic groups are selected from succinimidyl esters, halo acetals, maleimides, or dihydroxyphenyl derivatives and combinations thereof. Most preferably, the n≥2 electrophilic groups are selected from maleimides or dihydroxyphenyl derivatives and combinations thereof.

According to a particularly preferred embodiment the m≥2 nucleophilic groups comprised in the NU-POX component of the cross-linked polymer are capable of reacting with the n≥2 electrophilic groups of the cross-linking agent under ambient and/or physiological conditions to form covalent bonds.

Non-reacted electrophilic groups in the cross-linked polymer of the present invention impart tissue adhesive properties to the polymer as they can react with nucleophilic groups (e.g amino groups and thiol groups) that are naturally present in tissue. Thus, when a cross-linked polymer containing non-reacted electrophilic groups is applied to tissue, the non-reacted electrophilic groups can react with nucleophilic groups of the tissue, thereby creating strong adhesion between the polymer and the tissue. The ability to form cross-links at ambient temperature is especially advantageous if the cross-linking should occur in situ during e.g. surgery. Typically, at 35° C. and 1 atm., the cross-linking reaction between the NU-POX and the cross-linking agent is completed within 30 minutes, preferably within 10 minutes, more preferably within 5 minutes, most preferably within 2 minutes.

The ability of the (dry) cross-linked polymer to swell when contacted with water, next to its overall hydrophobicity, depends strongly on the level of cross-linking. The more cross-linking, the lower the swelling index. Preferably, the polymer contains, per 100 monomers, not more than 50, more preferably not more than 20 and most preferably not more than 10 of covalent bonds that have been formed by the reaction between the nucleophilic groups of the NU-POX and the electrophilic groups of the cross-linking agent. Typically, this number of covalent bonds is at least 2 per 100 monomers.

NU-POX comprising pendant nucleophilic groups can suitably be prepared by cationic polymerization of 2-oxazoline monomers initiated by various electrophilic species, for example alkyl halides, sulfonic esters, strong acids and others. POX-derivatives containing activated groups in the side chain can be prepared directly from the 2-oxazoline monomer containing the required (protected) group, or by a polymer analogous reaction of polymer precursors. Synthesis of a functional group at the POX terminus is, for instance, described by Anna Mero et. al. (*Synthesis and characterization of poly*(*2-ethyl 2-oxazoline*)-*conjugates with proteins and drugs: Suitable alternatives to PEG-conjugates*?, Journal of Controlled Release 125 (2008) 87-95).

NU-POX containing ethyl and amino (—$NH_2$) groups in the alkyl side chain can be synthesized by reaction of poly[2-(ethyl/3-butenyl)]-2-oxazoline copolymer with cysteamine, by copolymerization of a protected amine monomer with 2-ethyl-2-oxazoline or by partial hydrolysis of POX followed by post-modification.

NU-POX containing ethyl and thiol (—SH) groups in the alkyl side chain can be prepared in a similar fashion by reaction of poly[2-(ethyl/3-butenyl]-2-oxazoline copolymer with an excess of ethanedisulfide, by copolymerization of 2-ethyl-2-oxazoline with a monomer bearing a protected thiol group or by partial hydrolysis of POX followed by post-modification.

In case the present cross-linked polymer is obtained by cross-linking an NHS-activated cross-linking agent, biodegradability can range from essentially non-degradable to easily degradable. Biodegradability can be improved by incorporation of an ester link that is more readily hydrolyzed than the secondary amides resulting from reactions between the NHS-ester and amines. The ester groups are directly hydrolyzed in aqueous environment by reaction with water while the secondary amides are mainly hydrolyzed by enzymatic degradation that will be very slow in the cross-linked network, at neutral pH.

Cationic polymerization enables the synthesis of copolymers with a predefined number of activated groups. Furthermore, cationic 2-alkyl-2-oxazoline polymerization can be used to incorporate a large number of active groups as these active groups are coupled to the numerous alkyl side chains of the POX. This again makes it possible to produce highly cross-linked polymers with excellent cohesive properties as well as outstanding adhesive properties in case the cross-linked polymer has a high density of unreacted electrophilic groups.

In addition, cationic polymerization allows the incorporation of various functional groups in the side-chain and/o terminus, thereby enhancing the versatility of the POX polymer system.

The synthesis of a copolymer containing a predefined number of activated groups per copolymer can be carried out as follows: a copolymer is synthesized by cationic polymerization of ETOX and BUTOX, as described previously, to yield a poly[2-(ethyl/3-butenyl)-2-oxazoline copolymer. Upon functionalization of the activated side chains with e.g. cysteamine, primary amine groups are introduced. In case the initial ETOX/BUTOX molar ratio is 90/10, the percentage of reactive groups per poly[2-(ethyl/3-butenyl)]-2-oxazoline copolymer, will be 10%. Increasing the BUTOX in the initial 90/10 ETOX/BUTOX mixture will eventually result in a higher percentage of amino groups, i.e. more than 10%. The exact number of incorporated amino groups can be controlled by the ratio of monomer to initiator that determines the length of the polymer. For example, using an ETOX/BUTOX ratio of 90/10 and a monomer to initiator ratio of 100:1 yields polymers with 100 repeat units comprising 10 amino groups. When the monomer to initiator ratio is changed to 200:1 the resulting copolymer will have 20 amino groups with the same ETOX/BUTOX ratio.

The cross-linked polymer of the present invention may be biodegradable or non-biodegradable. Preferably, the polymer is biodegradable.

The medical product of the present invention preferably comprises at least 25% and most preferably 50-100% by weight of dry matter of a cross-linked polymer as defined herein before. Preferred examples of such medical products include implants, tissue sealants, adhesive tissue tape, adhesive tissue film (sheet), suture material, polymer coated stents and haemostatic (porous) materials.

The medical product may suitable contain other pharmaceutically acceptable components besides the cross-linked polymer. For instance, it may be advantageous to incorporate a polymer that is not part of the cross-linked polymer. Examples of such polymers include aphipathic polymers (such as collagen, gelatin and fibrin), neutral biopolymers (such as dextran and agarose) or ionic polymers. The ionic polymers may be cationic (such as chitin or chitosan) or anionic. A suitable anionic polymer is, for example, a synthetic polymer, biopolymer or modified biopolymer comprising carboxy, sulfo, sulfato, phosphono or phosphato groups or a mixture thereof, or a salt thereof, for example a biomedical acceptable salt. Examples of synthetic anionic polymers are: a linear polyacrylic acid (PAA), a branched polyacrylic acid, for example a Carbophil® or Carbopol® type from Goodrich Corp., a poly-methacrylic acid (PMA), a polyacrylic acid or polymethacrylic acid copolymer, for example a copolymer of acrylic or methacrylic acid and a further vinylmonomer, for example acrylamide, N.N-dimethyl acrylamide or N-vinylpyrrolidone, a maleic or fumaric acid copolymer, a poly(styrenesulfonic acid) (PSS), a polyamido acid, for example a carboxy-terminated polymer of a diamine and a di- or polycarboxylic acid, for example carboxy-terminated Starburst™ PAMAM dendrimers (Aldrich), a poly(2-acrylamido-2-methylpropanesulfonic acid) (poly-(AMPS)), or an alkylene polyphosphate, alkylene polyphosphonate, carbohydrate polyphosphate or carbohydrate polyphosphonate, for example a teichoic acid. Examples of anionic biopolymers or modified biopolymers are: hyaluronic acid (HA), modified HA (esterified HA or amine modified HA), glycosamino-glycanes such as heparin or chondroitin sulfate, fucoidan, poly-aspartic acid, polyglutamic acid, carboxymethyl cellulose, carboxymethyl dextranes, alginates, pectins, gellan, carboxyalkyl chitins, carboxymethyl chitosans, sulfated polysaccharides. Preferred anionic biopolymers are alginic acid, hyaluronic acid.

The cross-linked polymer can be formed into shape by solvent casting, hot melt extrusion or electrospinning. It is also feasible to shape the cross-linked polymer by means of compression between two heated plates as described, for instance, in WO 2007/099370. The cross-links between the nucleophilic groups of the NU-POX and the electrophilic groups of the crosslinking agent provide cohesion and the excess of electrophilic groups enables the cross-linked polymer to form links to tissue. Thus, the present invention enables the preparation of medical products that combine cohesiveness with adhesiveness.

A very important property of POX films is that upon thorough drying to remove water they protect the interior from hydrolysis. Thus, excess (non-reacted) electrophilic groups in the crosslinked polymer will retain their activity upon storage. When a medical product containing non-reacted electrophilic groups is applied to tissue an electrophilic-nucleophilic reaction will occur between these electrophilic groups and nucleophilic reactants, notably amino or thiol groups present in tissue, thereby forming a cross linked external network (adhesion) via covalent bonding. Accordingly, the medical product advantageously is a dehydrated product containing less than 10%, even more preferably less than 5% and most preferably less than 1% water by weight of the cross-linked polymer.

The medical product preferably contains not more than a limited amount of organic solvent. Preferably, the product contains less than 5%, more preferably less than 0.5% organic solvent by weight of the cross-linked polymer.

For e.g. a tissue sealing tape or film, NU-POX and cross-linking agent can be mixed in any ratio needed by solvent casting or hot melt extrusion. This approach enables very precise fine tuning of the properties needed for an adhesive tissue tape or film. In case the amount of nucleophilic groups in the NU-POX is low and the number of electrophilic groups provided by the cross-linking agent is relatively high, cohesion of the resulting cross-linked polymer will be low and adhesion to tissue will be high. Naturally, it is also feasible to produce an adhesive tissue tape or film with high cohesion and high adhesion by combining a NU-POX having a high density of nucleophilic groups with an excess amount of electrophilic cross-linking agent.

A particularly advantageous embodiment of the present medical product is an adhesive tissue tape or an adhesive tissue film. The present invention enables the preparation of a tape or film with excellent tissue-adhesive properties due to the presence of non-reacted electrophilic groups that are capable of reacting with nucleophilic groups naturally present in tissue. Furthermore, the cross-linked polymer of the present invention, due to its amorphous properties and tunable glass transition temperature, enables the preparation of cohesive, flexible and resilient tapes and films as well as tough and harder materials tailor-made for specific applications.

The tape or film according to the present invention may be non-permeable or permeable. Non-permeable tapes or films may suitably be used to seal off tissue, e.g. to prevent infection or dehydration. Permeable tapes or films may advantageously be employed to staunch bleeding from surgical or traumatic wounds. As explained herein before it is highly advantageous if the cross-linked polymer contained in the medical product is in an amorphous state. The term "amorphous" refers to a material that is a solid and in which there is no long-range order of the positions of the molecules. This lack of order distinguishes amorphous solids from crystalline solids.

The present invention enables the preparation of an amorphous tape or an amorphous film as the NU-POX component of the cross-linked polymer has excellent amorphous properties. These amorphous characteristics can be retained in the cross-linked polymer especially if the electrophilic cross-linking agent is a low molecular weight cross-linker as defined herein before.

It is further preferred that the cross-linked polymer in the medical product has a glass transition temperature of at least 0° C. and most preferably at least 20° C. Typically, the glass transition temperature of the polymer does not exceed 120° C.

The adhesive tissue tape or adhesive tissue film of the present invention offers the advantage that it can absorb substantial quantities of water to form a cohesive hydrogel. The absorption of water may result in significant swelling of the product. However, it is also possible to design the product in such a way that it does not swell significantly when it is brought into contact with moisture.

In accordance with an advantageous embodiment, the adhesive tissue tape or adhesive tissue film as described herein before does not exhibit significant swelling when it comes into contact with moisture. Typically, these medical products have a swelling index of between 0% and not more than 100%, preferably of between 0% and not more than 30%, and most preferably of between 0% and not more than 10%. Medical products having a low swelling index can suitably be applied in repair of dural defects and spinal cord repair.

Greater cross-linking creates a tighter network, which will decrease swelling. This can be advantageous in certain applications, for example, if the medical product is an implant, a suture material or a tissue sealant that is applied in tight locations where gel swelling can potentially cause adverse effects. In that case, the swelling index preferably does not exceed 50%, most preferably it does not exceed 10%.

The present invention enables the preparation of an adhesive tissue tape or tissue film having excellent properties without requiring, for instance, support layers. Accordingly, the adhesive tissue tape preferably is a single layer tape. Likewise, the adhesive tissue film preferably is a single layer film.

According to another embodiment of the invention, the medical product is a porous haemostatic product. Such a porous haemostatic product may be prepared, for instance, by converting a viscous solution of NU-POX into a foam and subsequently fixating the foam structure by cross-linking the NU-POX with the electrophilic cross-linking agent. Next, the solvent can be removed and a porous haemostatic product is obtained. Naturally, foaming agents and/or fillers can be employed in this process. Advantageously, the haemostatic product so obtained has tissue-adhesive properties due to the presence of non-reacted electrophilic groups as described herein before.

The haemostatic product may suitably contain a carrier, preferably a water-soluble carrier. Examples of carriers that may suitably be employed include monosaccharides; di- and oligosaccharides, such as lactose, mannitol, trehalose, erythritol, xylitol, sorbitol, maltitol, isomalt, maltodextrin, cellobiose, glucose, fructose, maltulose, lactulose, maltose, gentobiose, isomaltose, lactitol, palatinitol, dulcitol, ribitol, sucrose, raffinose, gentianose, planteose, verbascose, stachyose, melezitose, inositol; and polysaccharides, such as dextran, starch (amylose, amylopectin), glycogen, cellulose, chitin, alginates, callose, chrysolaminarin, xylan, arabinoxylan, mannan, fucoidan and galactomannan; and combinations of these carbohydrates. Preferably, the carrier employed has a glass transition temperature of at least 0° C., more preferably of at least 25° C.

Typically, the haemostatic product contains 25-75 wt. % of the NU-POX, 25-75 wt. % of the electrophilically activated cross-linking agent and 0-50 wt. % of carrier.

In accordance with another advantageous embodiment, the present medical product is an implant. According to a particularly preferred embodiment, the cross-linked polymer contained in the implant provides a matrix to support tissue regeneration. Preferably, this is a biodegradable three-dimensional bioresorbable porous construct with attaching properties to bone material and appropriate mechanical properties to guide cellular attachment and subsequent tissue formation. For bone reconstruction, the construct is preferably also load bearing, meaning that any fluid component in the implant, or the in-situ formed implant, should be kept as low as possible. In this respect it is advantageous that only very limited amounts of plasticizers like triacetin or water are needed to render the cross-linking agent and NU-POX extrudable.

According to an advantageous embodiment, the polymer network comprised in the present implant contains osteoconductive fillers like bone graft materials, including autologous bone, autologous bone particulate, allogenic bone graft material, human cadaver bone, xenograft bone graft material, animal bone, growth factors or synthetic materials such as hydroxyapatite, tricalcium phosphate and bioactive glass.

The medical product of the present invention may suitably be produced in the form of fibres or a fibrous fleece. This may be achieved, for instance, by means of electrospinning or by injecting a NU-POX containing fluid into a solution containing a high concentration of the electrophilic cross-linking agent. A fibrous fleece may be produced by employing a polymeric electrophilic cross-linking agent, such as dextran aldehyde, to produce the cross-linked polymer in solution and by subsequently removing the solvent (e.g. water) by means of evaporation. Fibrous fleeces can also be produced with the help of an anionic polymeric cross-linking agent such an alginate. This may be done, for instance, by preparing a solution of NU-POX and propylene glycol alginate at low pH and by subsequently increasing the pH, thereby initiating the cross-linking reaction.

A further aspect of the invention relates to a biocompatible, covalently cross-linked polymer that is obtained by reacting NU-POX with an electrophilic cross-linking agent other than an electrophilically activated polyoxazoline, said NU-POX comprising m nucleophilic groups; and said electrophilic cross-linking agent comprising n electrophilic groups, wherein the m nucleophilic groups are capable of reaction with the n electrophilic groups to form covalent bonds; wherein m≥2, n≥2 and m+n≥5; wherein the NU-POX comprises at least 30 oxazoline units in case the electrophilic cross-linking agent is an isocyanate; and wherein the total number of reacted and unreacted electrophilic groups contained in the polymer exceeds the total number of reacted and unreacted nucleophilic groups contained in the polymer by at least 3%, preferably at least 5%.

The covalently cross-linked polymer preferably is a cross-linked polymer as defined herein before.

Another aspect of the invention relates to a kit for producing the biocompatible, cross-linked polymer, said kit comprising NU-POX and the electrophilically activated cross-linking agent as defined herein before, wherein the kit comprises separately packaged volumes of the NU-POX and the electrophilic cross-linking agent, and wherein each of the NU-POX and the electrophilic cross-linking agent is present in the form of a fluid or reconstitutable powder.

Independently, the NU-POX and the electrophilic cross-linking agent may be provided in the form of fluid or a powder. Providing NU-POX and the cross-linking agent in the form of a fluid or reconstitutable powder allows the NU-POX and the cross-linking agent to undergo a rapid cross-linking reaction.

Preferably, the NU-POX is provided in the form of a fluid. More specifically, it is preferred that the NU-POX is contained in a first solvent in a concentration of 1-95 wt. %, preferably of 1.5-20%, most preferably of 2-10%. The electrophilic cross-linking agent is preferably also provided in the form of a fluid. Even more preferably, the electrophilically activated cross-linking agent is contained in a second solvent in a concentration of 1-95 wt. %, preferably of 1.5-30%, preferably of 2-10%.

In an embodiment in which both the NU-POX and the cross-linking agent are provided in the form of a fluid, said fluid may be a liquid or a viscous fluid. It is advantageous to employ both the NU-POX and the cross-linking agent in the form of a liquid of low viscosity in case both these components are to be applied, for instance, by spraying. In order to provide the NU-POX in the form of a low viscosity liquid, the NU-POX may need to be diluted substantially. In case a dilute liquid NU-POX solution is employed it is advisable to provide the cross-linking agent in a concentrated solution so as to achieve sufficient cross-linking. This may be achieved by employing a low molecular cross-linking agent as such cross-linking agents can be dissolved in high concentrations without causing high viscosities.

In case the NU-POX and the cross-linking agent are to be applied in a way that does not require these components to be low viscosity liquids, e.g. if they are applied by means of a dual syringe with, optionally, a static mixer, both the NU-POX and the cross-linking agents may be provided in the form of viscous (gelled) fluids.

According to another particularly preferred embodiment, the first solvent and the second solvent are selected from water, polyols, alcohols (e.g. ethanol or iso-propanol) and combinations thereof. The volume containing NU-POX and/or the volume containing the cross-linking agent advantageously contain polyol, water or a mixture of both. Furthermore, the latter volumes may suitably be buffered. The solvent(s) and buffering system employed in the present kit are suitable chosen so as to achieve an optimum cross-linking rate.

Polyols that can suitably be employed in the present kit include glycerol, diacetin, triacetin, sorbitol and combinations thereof.

According to a particularly preferred embodiment the first solvent and the second solvent contain 5-50 wt. % water, more preferably 10-30 wt. % water and most preferably 15-20 wt. % water.

The separately packaged volumes of the NU-POX and the electrophilically activated cross-linking agent may suitably contain a pH modifier.

The separately packaged volume containing the NU-POX preferably contains an alkalinizing agent that shifts the micro-environmental pH of the NU-POX containing volume to more alkaline conditions in the presence of water or bodily fluids.

Examples of suitable alkalinizing agents include ammonia solution, ammonium carbonate, alkali metal salts including alkali metal carbonates (for instance potassium carbonate and sodium carbonate), potassium hydroxide, sodium hydroxide and sodium borate (borax), tertiary amines such as triethylamine, triethanolamine, other amines like diethanolamine and monoethanolamine, and phosphates.

Preferably, the alkalinizing agent has a $pK_a$ at 25° C. of 8-14, in particular of 8.5-11, more particularly of 9 to 11.

The pH of the separately packaged volume containing NU-POX preferably lies in the range of 7-12, more preferably of 8-11, most preferably of 9-10.

The separately packaged volumes of the NU-POX and of the cross-linking agent are advantageously contained within a dispensing means from which both volumes can be dispensed simultaneously. Thus, the two agents may be delivered simultaneously and a cross-linked polymer will form in situ. By simultaneously dispensing the two reactants and delivering them at the site where they cross-linking should occur, pre-mixing can be avoided and premature cross-linking is effectively prevented. Examples of suitable dispensing means include spray dispensers, syringes, and dual syringes. Syringes suitably comprise a static mixer and/or a spray nozzle to ensure that the two reactants are mixed together when simultaneously expelled from said syringe.

In accordance with a preferred embodiment at least one of the separately packaged volumes contains a visualization agent to enhance the visibility. The visualization agent (e.g. a colourant) reflects or emits light at a wavelength detectable to a human eye. Because of the inclusion of the visualization agent it is easy for users to accurately apply the reactive mixture. Examples of suitable colourants include FD&C and D&C colorants, such as FD&C Violet No. 2, FD&C Blue No. 1, D&C Green No. 6, D&C Green No. 5, D&C Violet No. 2; and natural colorants such as beetroot red, canthaxanthin, chlorophyll, eosin, saffron, carmine, indocyanine green, or colored dyes normally found in synthetic surgical sutures. Similarly, dyes such as fluoroscein and methylene blue can be used. The visualization agent may or may not become chemically bound to the hydrogel.

In an alternative embodiment, the kit comprises a first biocompatible thin film containing the NU-POX and a second biocompatible thin film containing the electrophilically activated cross-linking agent. The two films may suitably be applied after combining the two films on top of each other. Films may suitably have been perforated to increase their specific surface area.

The biocompatible thin film containing the NU-POX preferably comprises an alkalinizing agent as defined herein before.

Yet another aspect of the invention concerns a kit for producing a biocompatible, cross-linked polymer, said kit comprising NU-POX and the electrophilic cross-linking agent as defined herein before, wherein the kit comprises a powder consisting of particles having a weight averaged mean diameter of 0.01-1000 µm, said particles including particles containing NU-POX and particles containing the electrophilic cross-linking agent.

If the NU-POX or the electrophilic cross-linking agent is provided in powder form, the powder should be readily dispersible in a fluid which may be contained within the same kit.

The particles comprised in the kit preferably have a weight averaged mean diameter of 0.5-500 µm and most preferably of 2-300 µm, said particles including particles containing NU-POX and particles containing the electrophilically activated cross-linking agent. The NU-POX and the electrophilically activated cross-linking agent may be contained in the same particles or they may be contained in different particles within the same powder.

The aforementioned powder may suitably be used as a haemostatic powder that can be stored under ambient conditions.

Besides the NU-POX and/or the electrophilic cross-linking agent, the particles comprised in the haemostatic powder may suitably contain a carrier, preferably a water-soluble carrier. Examples of carriers that may suitably be employed include monosaccharides; di- and oligosaccharides, such as lactose, mannitol, trehalose, erythritol, xylitol, sorbitol, maltitol, isomalt, maltodextrin, cellobiose, glucose, fructose, maltulose, lactulose, maltose, gentobiose, isomaltose, lactitol, palatinitol, dulcitol, ribitol, sucrose, raffinose, gentianose, planteose, verbascose, stachyose, melezitose, inositol; and polysaccharides, such as dextran, starch (amylose, amylopectin), glycogen, cellulose, chitin, alginates, callose, chrysolaminarin, xylan, arabinoxylan, mannan, fucoidan and galactomannan; and combinations of these carbohydrates. Preferably, the carrier employed has a glass transition temperature of at least 0° C., more preferably of at least 25° C.

Typically, the haemostatic powder contains 25-75 wt. % of the NU-POX, 25-75 wt. % of the electrophilically activated cross-linking agent and 0-50 wt. % of carrier.

The cross-linked polymer that can be produced with the present kits may or may not have tissue-adhesive properties. For some applications it is beneficial if the kit can be used to produce a cross-linked polymer with tissue-adhesive properties. Thus, advantageously, the cross-linking agent contained in the present kit comprises an excess amount of electrophilic groups relative to the amount of nucleophilic groups contained in the NU-POX. Thus, the NU-POX and the electrophilically activated cross-linking agent can react to form a cross-linked polymer as defined herein before.

In-situ cross-linking characteristics of the present kits can be improved by plasticizing NU-POX with a plasticizer selected from the group of triacetin, glycerol, triethylamine and combinations thereof. Typically, the plasticizer is employed in a concentration of 1-50%, more preferably 3-15% by weight of the NU-POX.

As explained herein before, a particularly preferred embodiment of the present kit produces a cross-linked polymer with tissue adhesive properties. This advantageous embodiment may be realized, for instance, by plasticizing NU-POX and the electrophilic cross-linking agent into a single film or tape. Before application as a tissue tape, the latter tape may be combined with another water soluble film containing an activator, or a fluid or a spreadable composition containing an activator.

The biocompatible cross-linked polymer according to the present invention as well as the NU-POX may advantageously contain an antimicrobial agent covalently bound to one of the oxazoline unit comprised therein. More preferably, the crosslinked polymer or NU-POX contains an antimicrobial agent that is covalently bound to oxazoline units through an amide or imide group. Examples of antimicrobial agents include aminophenols, aminocresol, amino resorcinol and aminonaphtol. The antimicrobial agent may suitably be bound to the POX-polymer via a spacer group, such as an alkylene, oxyalkylane or silicone. By covalently binding an antimicrobial agent to the POX-polymer it can be ensured that the antimicrobial agent is slowly released during biodegradation of the polymer.

The biocompatible cross-linked polymer may suitably further comprise one or more additive components selected from fillers, oxidants, crosslinkers, microgels, additional polymers, drugs and other therapeutic agents.

The medical products according to the present invention may advantageously be used in a variety of surgical applications. Examples of these surgical applications are summarized below.

| | |
|---|---|
| Neurosurgery | Repair of dural defects; repair of central nervous system tissue; spinal cord repair; nerve grafting; intervertebral disc surgery and cerebrospinal fluid leaks (CSF leaks). |
| Ophthalmic surgery | Clear corneal cataract surgery; laser in situ keratomileusis (LASIK) surgery; corneal ulcer treatment; corneal transplantation; conjunctival repair; retinal attachment; punctal plugging for treatment of dry eyes; oculoplastics and blepharoplasty (eyelid lifts); vitrectomy closure and attachment of extraocular muscles. |
| Ear, nose and throat surgery | Control of epistaxis (nosebleeds); repair of vocal cord defects; tympanoplasty for repair of perforated eardrum; myringotomy (eardrum incision for drainage) with tube insertion; sinus surgery; nasal reconstructive surgery; tonsillectomy surgery and adenoidectomy surgery. |
| Head and neck surgery | Salivary gland removal; lymph node dissection and treatment of chylous leakage after neck dissection. |
| Interventional radiology | Therapeutic embolization and femoral artery closure during interventional procedures. |
| Vascular surgery | Arteriovenous fistula repair, aortic aneurysm repair and vascular anastomosis. |

| | |
|---|---|
| Cardiovascular surgery | Cardiac valve repair; repair of ventricular wall rupture; coronary artery anastomosis during bypass surgery; pacemaker and lead placement; aortic anastomosis and treatment of aortic dissection. |
| Thoracic surgery | Lung lobectomy; lung biopsy and pneumothorax treatment. |
| Gastrointestinal surgery | gastrointestinal anastomosis; peptic ulcer treatment; treatment of esophageal rupture; gallbladder or bile duct anastomosis; gastric bypass surgery; appendectomy; cholecystectomy (gallbladder removal); pancreatic surgery; gastrointestinal fistula repair; sealing of peritoneal dialysis catheter leakage, treatment of abdominal hernias and prevention of intra-abdominal adhesions |
| Colorectal surgery | Colonic anastomosis; rectal fistula repair; treatment of diverticular bleeding; hernia patch placement and hemorrhoidectomy. |
| Liver surgery | Liver resection and liver transplantation. |
| Gynecologic surgery | Hysterectomy; myomectomy for uterine fibroid removal; fallopian tube anastomosis; vaginal fistula repair; cervical surgery; ovarian cyst removal; breast biopsy; mastectomy and lumpectomy and management of preterm premature rupture of membranes. |
| Urologic surgery | Nephrectomy, kidney transplantation; urethral fistula repair; urethral anastomosis; repair for stress urinary incontinence; bladder closure; radical prostatectomy and vasectomy reversal surgery. |
| Pediatric surgery | Congenital cleft lip repair |
| Orthopedic surgery | Hip replacement surgery; knee replacement surgery; tendon reattachment; cartilage repair; intervertebral disc repair, fracture repair and bone grafting |
| Plastic and reconstructive surgery | Face lift surgery; closure of skin incisions; soft tissue augmentation |
| Trauma surgery | Closure of splenic lacerations and other solid organs; closure of skin lacerations; bleeding control during burn debridement and skin grafting for burn victims. |

Polymeric coated gas bubbles acting as ultrasound contrast agents can suitably be embedded in the kits or the medical products described herein before. Polymeric coated gas bubbles derive their contrast properties from the large acoustic impedance mismatch between blood and the gas contained therein. Examples of polymers that can be used to coat these gas bubbles include polylactide, polyglycolide, polycaprolactone, copolymers of polylactide and polyglycolide, copolymers of lactide and lactone, polysaccharide, polyanhydride, polystyrene, polyalkylcyanoacrylate, polyamide, polyphosphazene, poly(methylmethacrylate), polyurethane, copolymers of methacrylic acid and acrylic acid, copolymers of hydroxyethylmethacrylate and methylmethacrylate, polyesters, such as polycarbonates, and protein. Preferred polymers are those which are biocompatible and/or biodegradable. In a preferred embodiment the polymer is polylactic co-glycolic acid (PLGA).

The invention is further illustrated by means of the following non-limiting examples.

EXAMPLES

Example 1

Amphiphilic copolymers of NU-POX containing ethyl and amine groups in the alkyl side chain were synthesized by controlled acidic hydrolysis of aquazol 50 (poly(2-ethyl-2-oxazoline (PEtOx), Mw 50,000) to yield a poly[2-ethyl-2-oxazoline/ethylene imine] copolymer (PEtOx-PEI). 12% of the initial 2-ethyl-oxazoline units was hydrolyzed.

This poly[2-ethyl-2-oxazoline/ethylene imine] was functionalized in a two-step approach by first coupling of methyl succinyl chloride, followed by the reaction of the methyl ester with ethylenediamine (30 equivalents in the absence of solvent) to yield an amine-side chain activated poly[2-(ethyl/amine-ethyl-amide-ethyl)-2-oxazoline] copolymer.

An amount of 1.31 mg of this $NH_2$-side chain activated poly[2-(ethyl/amine-ethyl-amide-ethyl)-2-oxazoline] copolymer was dissolved in a mixture of 50 µL ethanol (absolute), 104 water and 44 triethyl amine. A solution containing 20,000 Da N-hydroxy succinimide end capped PEG powder (DuraSeal Dural Sealant System) 8.76 mg in 50 µL water was added. The combined fluid mixture (about 115 µL with a $NH_2$:NHS ratio of 1:1.22) turned into a cross linked network (gel) within 30 seconds at room temperature.

Example 2

$NH_2$-side chain activated poly[(2-ethyl/amine-ethyl-amide-ethyl)-2-oxazoline] copolymer was synthesized as described in example 1.

An amount of 1.26 mg of this $NH_2$-side chain activated poly[2-(ethyl/amine-ethyl-amide-ethyl)-2-oxazoline] copolymer was dissolved in a mixture of 28 µL ethanol (absolute), 1.4 µL water and 0.2 µL triethyl amine. A solution containing 20,000 Da N-hydroxy succinimide end capped PEG powder (DuraSeal Dural Sealant System) 8.79 mg in 50 µL was added. The combined fluid mixture (about 80 µL with a $NH_2$:NHS ratio of 1:1.27) was poured onto a fresh dissected bovine peritoneum. The resulting hydrogel was found to adhere to the tissue.

Example 3

$NH_2$-side chain activated poly[(2-ethyl/amine-ethyl-amide-ethyl)-2-oxazoline] copolymer was synthesized as described in example 1.

An amount of 14.38 mg of this $NH_2$-side chain activated poly[2-(ethyl/amine-ethyl-amide-ethyl)-2-oxazoline] copolymer was dissolved in a mixture of 300 µL ethanol (absolute), 30 µL water and 5 µL triethyl amine and 3.69 mg of ethyl ester L-lysine diisocyanate (CAS 45172-15-4) was added. The combined fluid mixture (about 340 µL with a $NH_2$:NCO ratio of 1:2) turned into a cross linked network (gel) within 2 minutes.

Example 4

$NH_2$-side chain activated poly[(2-ethyl/amine-ethyl-amide-ethyl)-2-oxazoline] copolymer was synthesized as described in example 1.

An amount of 14.12 mg of this $NH_2$-side chain activated poly[2-(ethyl/amine-ethyl-amide-ethyl)-2-oxazoline] copolymer was dissolved in a mixture of 200 µL ethanol (absolute), 10 µL water and 1.4 µL triethyl amine and 3.69 mg of ethyl ester L-lysine diisocyanate (CAS 45172-15-4) was added. The combined fluid mixture (about 220 µL with a $NH_2$:NCO ratio of 1:2.11) turned into a cross linked network (gel) within 20 seconds. The gel was placed onto a fresh dissected bovine peritoneum and was found to adhere to the tissue.

Example 5

$NH_2$-side chain activated poly[(2-ethyl/amine-ethyl-amide-ethyl)-2-oxazoline] copolymer was synthesized as described in example 1.

An amount of 14.92 mg of this $NH_2$-side chain activated poly[2-(ethyl/amine-ethyl-amide-ethyl)-2-oxazoline] copolymer was dissolved in a mixture of 350 µL ethanol (absolute), 10 µL water and 5 µL triethyl amine and this solution was added to a solution containing 5.17 mg propylene glycol alginate (PGA) in 205 µL water. The combined fluid mixture (about 570 µL with a $NH_2$:propylene glycol ratio of 1:1.35) turned into a cross linked network (gel) within 10 minutes.

Example 6

$NH_2$-side chain activated poly[(2-ethyl/amine-ethyl-amide-ethyl)-2-oxazoline] copolymer was synthesized as described in example 1.

An amount of 14.72 mg of this $NH_2$-side chain activated poly[2-(ethyl/amine-ethyl-amide-ethyl)-2-oxazoline] copolymer was dissolved in a mixture of 200 µL ethanol (absolute), 10 µL water and 1.4 µL triethyl amine and this solution was added to a solution containing 5.59 mg propylene glycol alginate (PGA) in 205 µL water. The combined fluid mixture (about 420 µL with a $NH_2$:propylene glycol ratio of 1:1.46) was poured onto a fresh dissected bovine peritoneum. The resulting hydrogel was found to adhere to the tissue.

Example 7

$NH_2$-side chain activated poly[(2-ethyl/amine-ethyl-amide-ethyl)-2-oxazoline] copolymer was synthesized as described in example 1.

To a solution of 1 g dextran, MW 9,000-11,000 in 9 mL water, cooled to 0° C., a solution of 1 g sodium periodate in 9 mL water was added dropwise. After addition had been completed, the mixture was stirred for 4 hours at room temperature. Next, 328 mg of $CaCl_2$ was added and stirred for 30 minutes and filtered. The resulting filtrate was combined with 350 mg potassium iodide and stirred for 30 minutes. The resulting red solution was added dropwise to 200 mL cold acetone and the agglomerated product was separated. The white solid was dissolved in water and freeze-dried, resulting in a white dextran aldehyde (MW 9,000-11,000) of which about 50% of the glucopyranose rings oxidatively cleaved to dialdehydes.

An amount of 7.87 mg of the $NH_2$-side chain activated poly[2-(ethyl/amine-ethyl-amide-ethyl)-2-oxazoline] copolymer was dissolved in a mixture of 150 µL ethanol (absolute), 15 µL water and 2.5 µL triethyl amine and this solution was added to a solution containing 12.07 mg dextran aldehyde in 150 µL water. The combined fluid mixture (about 320 µL with a $NH_2$:aldehyde ratio of 1:8.68) turned into a cross linked network (gel) within 30 seconds.

Example 8

$NH_2$-side chain activated poly[(2-ethyl/amine-ethyl-amide-ethyl)-2-oxazoline] copolymer was synthesized as described in example 1.

Dextran aldehyde was synthesized as described in example 7.

An amount of 7.28 mg of this $NH_2$-side chain activated poly[2-(ethyl/amine-ethyl-amide-ethyl)-2-oxazoline] copolymer was dissolved in a mixture of 100 µL ethanol (absolute), 5 µL water and 0.7 µL triethyl amine and this solution was added to a solution containing 12.72 mg dextran aldehyde in 150 µL water. The combined fluid mixture (about 260 µL with a $NH_2$:aldehyde ratio of 1:9.89) was poured onto a fresh dissected bovine peritoneum. The resulting hydrogel was found to adhere to the tissue.

Example 9

2-(2-Methoxycarbonylethyl)-2-oxazoline was prepared following a literature procedure (M. T. Zarka, O. Nuyken, R. Weberskirch, Chem. Eur. J. 2003, 9, 3228-3234, a modified procedure of A. Levy, M. Litt, J. Polym. Sci. A 1968, 6, 1883) followed by cationic ring-opening polymerization yielding the corresponding methylester functionalized homopolymer, poly(2-(2-methoxycarbonylethyl)-2-oxazoline).

Homopolymerization of the 2-(2-methoxycarbonylethyl)-2-oxazoline monomer yielded poly(2-(2-methoxycarbonylethyl)-2-oxazoline) homopolymer.

Copolymerization of the 2-(2-methoxycarbonylethyl)-2-oxazoline monomer with 2-ethyl-2-oxazoline (25, 50 and 75%) or 2-methyl-2-oxazoline (25, 50 and 75%) yielded statistical copolymers.

The poly[2-(2-methoxycarbonylethyl)-2-oxazoline] homopolymer was reacted with N-Boc amino ethane amine by dissolving 0.8 g polymer in 2.5 mL N-Boc amino ethane amine followed by 23 hours stirring at 80° C. $^1$H NMR spectroscopy in $CDCl_3$ revealed that ~90% of the methyl ester units were converted into Boc-aminoethyl amido side chains. This polymer was further reacted with hydrochloric acid (HCl) by dissolving 850 mg of polymer in dichloromethane (30 mL), which was added dropwise to a HCl solution in ethyl acetate (0.175 mL, 2.98 mmol). After complete addition, the solution was stirred for 6 hours at room temperature. $^1$H NMR spectroscopy demonstrated the successful formation of the hydrochloric acid salt of aminoethyl amido side chain functionalized polymer by disappearance of the Boc signal at 1.4 ppm to yield >90% amine-side chain activated poly[2-(amine-ethyl-amide-ethyl)-2-oxazoline] copolymer (NU-POX).

The copolymer of 2-ethyl-2-oxazoline containing 25% 2-methoxycarbonyl ethyl-2-oxazoline was functionalized by the reaction of the methyl ester side chains with ethylenediamine (30 equivalents in the absence of solvent) to yield exactly 25% amine-side chain activated poly[2-(ethyl/amine-ethyl-amide-ethyl)-2-oxazoline] copolymer (NU-POX).

The copolymer of 2-methyl-2-oxazoline containing 25% 2-methoxycarbonyl ethyl-2-oxazoline was functionalized by the reaction of the methyl ester side chains with ethylenediamine (30 equivalents in the absence of solvent) to yield exactly 25% amine-side chain activated poly[2-(methyl/amine-ethyl-amide-ethyl)-2-oxazoline] copolymer (NU-POX).

The poly[2-(2-methoxycarbonylethyl)-2-oxazoline] homopolymer was functionalized in two-step approach by partial hydrolysis (25, 50 and 75%) with LiOH of the methylester to the carboxylic acid, followed by activation of the obtained carboxylic acid moieties with NHS in the presence of diisopropyl carbodiimide and triethylamine to synthesize NHS-side chain activated poly(NHS-ester-ethyl-oxazoline/methoxycarbonylethyl oxazoline) copolymer (EL-POX). The final functionalization degree with NHS was confirmed by UV-Vis spectroscopy and $^1$H NMR spectroscopy to be very close to 25, 50 and 75%.

Copolymers of 2-ethyl-2-oxazoline containing 25, 50 or 75% methylester units and copolymers of 2-methyl-2-oxazoline containing 25, 50 or 75% methylester units were functionalized in two-step approach by quantitative hydrolysis with LiOH of the methylester to the carboxylic acid, followed by activation of the obtained carboxylic acid moieties with NHS in the presence of diisopropyl carbodiimide and triethylamine to synthesize NHS-side chain activated poly[2-(NHS-ester-ethyl)-2-oxazoline] polymer (EL-POX). The final functionalization with NHS was confirmed by UV-Vis spectroscopy and $^1$H NMR spectroscopy to be exactly 25, 50 and 75%.

Example A

Not According to the Claimed Invention

Polymers of EL-POX containing NHS groups in the alkyl side chain were synthesized by >95% acidic hydrolysis of Aquazol-50 (poly(2-ethyl-2-oxazoline, PEtOx, Mn 50,000) to yield linear poly(ethylene imine) (LPEI). LPEI was functionalized in a two-step approach by coupling of succinic anhydride in DMSO, followed by activation of the obtained carboxylic acid moieties with NHS in the presence of diisopropyl carbodiimide and triethylamine to synthesize NHS-side chain activated poly(NHS-ester-ethyl-oxazoline) polymer. The final functionalization with NHS was confirmed by UV-Vis spectroscopy and $^1$H NMR to be >95% (EL-POX). This compound was water insoluble.

LPEI was functionalized in an identical two-step approach with 25, 50 and 75% stoichiometric amounts of NHS, with reference to the carboxylic acid moieties, in the presence of diisopropyl carbodiimide and triethylamine to synthesize resp. 25, 50 and 75% NHS-side chain activated poly(NHS-ester-ethyl-oxazoline/carboxyethyl oxazoline) copolymers. The final functionalization degree with NHS was confirmed by UV-Vis spectroscopy and $^1$H NMR spectroscopy to be approximately 25, 50 and 75%. These EL-POX compounds were water soluble and soluble in 10/90 v/v % water/methanol, resp. water/ethanol mixtures.

An amount of 1.16 mg of the 25% amine-side chain activated poly[(2-ethyl/amine-ethyl-amide-ethyl)-2-oxazoline] copolymer described in Example 9 was dissolved in a mixture of 10 µL ethanol:triethyl amine (99:1) and this solution was added to a solution containing 8.84 mg of the 25% NHS-side chain activated poly[2-(2-methoxycarbonylethyl)/(2-ethyl-NHS esters)-2-oxazoline] copolymer in 70 µL ethanol. The combined fluid mixture (about 90 µL with a NHS:NH2 ratio of 5:1) turned into a cross linked network (gel) within 60 seconds.

This example illustrates that NU-POX can suitably be cross-linked with a NHS-functional polymer.

Example B

Not According to the Claimed Invention

Amine-side chain activated poly[2-(ethyl/NHS-ester-ethyl)]-2-oxazoline copolymer (NU-POX) was synthesized by controlled acidic hydrolysis of aquazol 50 (poly(2-ethyl-2-oxazoline (PEtOx), Mw 50,000) to yield a poly[2-ethyl-2-oxazoline/ethylene imine] copolymer (PEtOx-PEI) in which 12% of the initial 2-ethyl-oxazoline units was hydrolyzed.

This poly[2-ethyl-2-oxazoline/ethylene imine] was functionalized in a two-step approach by first coupling of methyl succinyl chloride in the presence of triethylamine, followed by the reaction of the formed methyl ester side chain with ethylenediamine to yield an amine-side chain activated poly(2-ethyl/amino-ethyl-amide-ethyl)-2-oxazoline copolymer.

This NU-POX was turned into an EL-POX by reacting the amine with maleic anhydride to yield maleimide-side chain activated poly(2-ethyl/maleimide-ethyl-amide-ethyl)-2-oxazoline copolymer.

POX containing >95% NHS moieties in the alkyl side chain was synthesized as described in Example A. This EL-POX was reacted with cysteamine hydrochloride to synthesize the thiol containing polymer which was cross-linked by disulfide bonds. The identity was confirmed by $^1$H NMR (NU-POX).

The disulfide bonds were reduced with tris(2-carboxyethyl) phosphine (TCEP). Crosslinking of the thiol side chain activated polymer (10 mg in 500 µL) was tested with maleimide-side chain activated poly(2-ethyl/maleimide-ethyl-amide-ethyl)-2-oxazoline copolymer (6 mg in 100 µL) in the presence of 100 µL triethylamine (TEA).

Crosslinking in 600 µL DMSO/MeOH (2:5 v/v) in the presence of TEA (100 µL) was confirmed using 6 mg EL-POX and 5 mg NU-POX from this example. A gel was formed within 20 seconds at room temperature.

Example C

Not According to the Claimed Invention

Polymers containing 2-thiazoline-2-thioesters in the alkyl side chain were synthesized by the following procedure.

POX containing >95% carboxylic acid moieties in the alkyl side chain was synthesized as described in Example A. This POX was activated with 2-thiazoline-2-thiol in the presence of diisopropyl carbodiimide and triethylamine to synthesize 2-thiazoline-2-thioester-side chain activated poly [2-(thiazoline-thioester-ethyl)-2-oxazoline] polymers (EL-POX). The identity of this EL-POX was confirmed by $^1$H NMR.

Amphiphilic copolymers of NU-POX containing ethyl and NH$_2$ groups in the alkyl side chain were synthesized as described in example 1:12% of the initial 2-ethyl-oxazoline units were hydrolyzed.

Crosslinking in 400 µL DMSO/MeOH (1:1 v/v) without addition of base was confirmed using 7.0 mg EL-POX and 15.8 mg NU-POX from this example. A gel was formed within 30 seconds at room temperature.

This example illustrates that NU-POX can suitably be cross-linked with a thiazoline-functional polymer.

Example D

Not According to the Claimed Invention

Polymers containing aldehyde functionalities in the alkyl side chain were synthesized by the following procedure.

EL-POX containing >95% N-hydroxysuccinimide (NHS) groups in the alkyl side chain was synthesized as described in Example A. This EL-POX was reacted with 2-(1,3-Dioxolan-2-yl)ethanamine to synthesize a polymer containing >95% protected aldehyde functionality. The polymer was deprotected using a previously described procedure (Taubmann, C., Luxenhofer, R., Cesana, S. and Jordan, R. (2005), First Aldehyde-Functionalized Poly(2-oxazoline)s for Chemoselective Ligation. Macromol. Biosci., 5: 603-612.) which yielded the >95% aldehyde functionalized polymer (EL-POX). The identity was confirmed by $^1$H-NMR and $^{13}$C-NMR.

Crosslinking in 400 µL DCM/MeOH (1:1, v/v) without addition of base was confirmed using 7.0 mg EL-POX from this example and 15.8 mg NU-POX from example 1. A gel was formed within 60 seconds at room temperature.

This example illustrates that NU-POX can suitably be cross-linked with an aldehyde-functional polymer.

Example E

Not According to the Claimed Invention

NHS-side chain activated poly[2-(NHS-ester-ethyl)-2-oxazoline] copolymer, containing 50% NHS units and 25% amine-side chain activated poly[2-(ethyl/amine-ethyl-amide-ethyl)-2-oxazoline] copolymer were prepared as described in Example A.

The NHS-side chain activated poly[2-(NHS-ester-ethyl)-2-oxazoline] copolymer, containing 50% NHS units was dissolved in ethanol (absolute). Separately, the 25% amine-side chain activated poly[2-(ethyl/amine-ethyl-amide-ethyl)-2-oxazoline] copolymer was dissolved in ethanol (absolute). To both solutions a small amount of glycerol (plasticizer) had been added. The solutions were mixed for solvent casting and the mixture was dried to an amorphous tape by means of vacuum at room temperature.

The burst pressure of this formulation was tested in the following manner. Collagen casing of consistent properties and thickness (sausage casing, Nippi Casing Co. (#320),4) was used (substrate). Sections of the substrate were washed in deionized water to remove glycerine and soaked in fresh deionized water for five minutes. A 3 mm circular incision was cut into the substrate, which was then secured to a burette in such a manner that simulated body fluid could be forced out under measurable pressure via the circular incision.

The amorphous tape was put onto the secured substrate to form a seal. After a few minutes, the pressure of the simulated body fluid was increased to the point that the seal burst (burst pressure). The burst pressure was found to be adequate for a sealing tape. The NHS:amine ratio in this film was 5:1.

Example F

Not According to the Claimed Invention

A syringe comprising two separate reservoirs and a static mixing unit to mix the contents of the reservoirs when the two reservoirs are emptied simultaneously was filled with two viscous fluids.

NH2-side chain activated poly[(2-ethyl/amine-ethyl-amide-ethyl)-2-oxazoline] copolymer (NU-POX) was synthesized as described in example 1 and 75% NHS-side chain activated poly(NHS-ester-ethyl-oxazoline) polymer (EL-POX) was prepared as described in example A.

The NU-POX was weighed accurately into a vessel containing water and the contents (50/50 w/w) were mixed well. The first reservoir of the syringe was filled with the NU-POX gel taking care to exclude large air bubbles. The second reservoir of the syringe was filled with an aqueous EL-POX solution that had been prepared in an identical manner. The amine-NHS ratio was 1:5.

Both the static mixer and plunger were attached and the two gels were extruded through the static mixture to form a homogenous, clear, cross linked polymeric phase with an initial setting time of less than 1 minute.

Example G

Not According to the Claimed Invention

The dual syringe experiment as described in example F was repeated. In this experiment however, the EL-POX was dissolved in glycerol 85% and the final amine-NHS ratio was 1:1.

Both the static mixer and plunger were attached and the two gels were extruded through the static mixture to form a homogenous, clear, cross linked polymeric phase with an initial setting time of less than 1 minute.

Example H

Not According to the Claimed Invention

NH2-side chain activated poly[(2-ethyl/amine-ethyl-amide-ethyl)-2-oxazoline] copolymer was synthesized as described in example 1 (NU-POX) and 75% NHS-side chain activated poly(NHS-ester-ethyl-oxazoline) polymer was synthesized as described in example A (EL-POX). N-hydroxy succinimide end capped PEG powder 20,000 Da [PEG-NHS] was obtained form a DuraSeal, Dural Sealant System and trilysine was purchased from Sigma. The number of electrophilic groups/molecule of EL-POX was approximately 375 and the number of electrophilic groups/molecule of PEG-NHS was approximately 4. The number of nucleophilic groups/molecule of NU-POX was approximately 29 and the number of electrophilic groups/molecule of trilysine was 4.

Separately, the NU-POX and the PEG-NHS were dissolved in water containing the same amount (w/w) of trehalose, snap freezed with the aid of liquid nitrogen and freeze dried overnight yielding respectively, NU-PDXt and PEG-NHSt.

The EL-POX was dissolved in water containing the same amount (w/w) of trehalose including citrate buffer (pH 5,5 after reconstitution in water), snap freezed with the aid of liquid nitrogen en freeze dried overnight yielding EL-PDXt. Trilysine was dissolved in water containing a 100 fold amount (w/w) of trehalose, snap freezed with the aid of liquid nitrogen en freeze dried overnight yielding trylisine-t.

1.0 mL of heparinized fresh, whole blood was added to the freeze dried formulations, and combinations thereof at room temperature and mixed to assess haemostatic properties (using the tube inversion test). The results of these experiments are depicted in Table 1. A carbonate-bicarbonate buffer (1 mg $Na_2CO_3$+13 mg $NaHCO_3$) was added in dry salt form to the freeze dried formulations prior to addition of the blood. Addition of the blood to the formulations with the carbonate/bicarbonate buffer resulted in a final pH of 9.

TABLE 1

| Exp. | EL-POXt (mg) | PEG-NHSt (mg) | NU-POXt (mg) | Trilysine-t (mg) | Time to haemostasis (min) |
|---|---|---|---|---|---|
| A | 49 | | | | 1.5 |
| B | 52 | | 9 | | 1.0 |
| C | | 49 | | 30 | >3 |

From these results it is clear that formulations A and B exhibited adequate haemostatic properties. Best results were obtained for the formulation containing a combination of NU-POX and EL-POX, indicating that the cross-linking imparted improved haemostatic properties. Furthermore, it was found that the cross-linking yielded a stronger gel. Without buffer, experiment B lead to a gel in about 15 minutes.

Experiment C did not lead to any gelation and/or haemostasis.

The invention claimed is:
1. A biocompatible tissue-adhesive medical product comprising at least 1% by weight of dry matter of a covalently cross-linked polymer that is obtained by reacting a nucleophilically activated polyoxazoline (NU-POX) with an electrophilic cross-linking agent other than an electrophilically activated polyoxazoline, said NU-POX comprising m nucleophilic groups; and said electrophilic cross-linking agent comprising n electrophilic groups, wherein the m nucleophilic groups are capable of reaction with the n electrophilic groups to form covalent bonds; wherein m≥2, n≥2 and m+n≥5; and wherein the NU-POX comprises at least 30 oxazoline units in case the electrophilic cross-linking agent is an isocyanate, and wherein the tissue-adhesive properties derive from a reaction of non-reacted electrophilic groups in the cross-linked polymer with nucleophilic groups present in the tissue.

2. The medical product according to claim 1, comprising at least 25% by weight of dry matter of the covalently cross-linked polymer.

3. The medical product according to claim 1, wherein the product is an adhesive tissue tape, an adhesive tissue film, a tissue sealant, a haemostatic material, a suture material, a polymer coated stent or an implant.

4. The medical product according to claim 1, wherein the cross-linked polymer contained in the medical product is in an amorphous state.

5. The medical product according to claim 1, wherein the total number of reacted and unreacted electrophilic groups contained in the polymer exceeds the total number of reacted and unreacted nucleophilic groups contained in the polymer by at least 3%.

6. The medical product according to claim 5, wherein the total number of reacted and unreacted electrophilic groups contained in the polymer exceeds the total number of reacted and unreacted nucleophilic groups contained in the polymer by at least 5%.

7. The medical product according to claim 1, wherein at least one of the m nucleophilic groups is a pendant nucleophilic group.

8. The medical product according to claim 7, wherein the NU-POX comprises 3 to 50 pendant nucleophilic groups per 100 monomers.

9. The medical product according to claim 1, wherein the m nucleophilic groups are selected from amine groups, thiol groups, phosphine groups and combinations thereof.

10. The medical product according to claim 9, wherein the nucleophilic groups are amine groups and the electrophilic groups contained in the electrophilic cross-linking agent are selected from carboxylic acid esters, sulfonate esters, phosphonate esters, thioesters, pentafluorophenyl esters, p-nitrophenyl esters, p-nitrothiophenyl esters, acid halide groups, anhydrides, ketones, aldehydes, isocyanato, thioisocyanato, epoxides, activated hydroxyl groups, glycidyl ethers, carboxyl, succinimidyl ester, succinimidyl carbonate, succinimidyl carbamates, sulfosuccinimidyl ester, sulfosuccinimidyl carbonate, imido esters, dihydroxy-phenyl derivatives, and combinations thereof.

11. The medical product according to claim 9, wherein the nucleophilic groups are thiol groups and the electrophilic groups contained in the electrophilic cross-linking agent are selected from halo acetals, orthopyridyl disulfide, maleimides, vinyl sulfone, dihydroxyphenyl derivatives, vinyl, acrylate, acrylamide, iodoacetamide, succinimidyl ester, succinimidyl carbonate, succinimidyl carbamates, sulfosuccinimidyl ester, sulfosuccinimidyl carbonate and combinations thereof.

12. The medical product according to claim 1, wherein the electrophilic cross-linking agent contains a backbone that carries or is substituted with n≥2 electrophilic groups, said backbone being selected from the group of polymers consisting of agar, starch, pullulan, inulin, levan, silk, fibronectin, pectin, cellulose collagen, elastin, gelatine, albumin, fibrin, fibrinogen, dextran, methyl cellulose, hyaluronic acid, chondroitin sulfate, keratosulfate, heparan sulfate, dermatan sulfate, alginic acid, chitosan, chitin, heparin, polyvinyl alcohol, polyethylene glycol and combinations thereof.

13. A biocompatible, tissue-adhesive, covalently cross-linked polymer that is obtained by reacting a nucleophilically activated polyoxazoline (NU-POX) with an electrophilic cross-linking agent other than an electrophilically activated polyoxazoline, said NU-POX comprising m nucleophilic groups; and said electrophilic cross-linking agent comprising n electrophilic groups, wherein the m nucleophilic groups are capable of reaction with the n electrophilic groups to form covalent bonds; wherein m≥2, n≥2 and m+n≥5; wherein the NU-POX comprises at least 30 oxazoline units in case the electrophilic cross-linking agent is an isocyanate; and wherein the tissue-adhesive properties derive from a reaction of non-reacted electrophilic groups in the cross-linked polymer with nucleophilic groups present in the tissue.

14. The biocompatible, cross-linked polymer according to claim 13, wherein the total number of reacted and unreacted electrophilic groups contained in the polymer exceeds the total number of reacted and unreacted nucleophilic groups contained in the polymer by at least 5%.

15. The biocompatible, cross-linked polymer according to claim 13, wherein at least one of the m nucleophilic groups is a pendant nucleophilic group.

16. The biocompatible, cross-linked polymer according to claim 15, wherein the NU-POX contains 3 to 50 pendant nucleophilic groups per 100 monomers.

17. The biocompatible, cross-linked polymer according to claim 13, wherein the m nucleophilic groups are selected from amine groups, thiol groups, phosphine groups and combinations thereof.

18. The biocompatible, cross-linked polymer according to claim 17, wherein the nucleophilic groups are amine groups and the electrophilic groups contained in the electrophilic cross-linking agent are selected from carboxylic acid esters, sulfonate esters, phosphonate esters, thioesters, pentafluorophenyl esters, p-nitrophenyl esters, p-nitrothiophenyl esters, acid halide groups, anhydrides, ketones, aldehydes, isocyanato, thioisocyanato, epoxides, activated hydroxyl groups, glycidyl ethers, carboxyl, succinimidyl ester, succinimidyl carbonate, succinimidyl carbamates, sulfosuccinimidyl ester, sulfosuccinimidyl carbonate, imido esters, dihydroxy-phenyl derivatives, and combinations thereof.

19. The biocompatible, cross-linked polymer according to claim 17, wherein the nucleophilic groups are thiol groups and the electrophilic groups contained in the electrophilic cross-linking agent are selected from halo acetals, orthopyridyl disulfide, maleimides, vinyl sulfone, dihydroxyphenyl derivatives, vinyl, acrylate, acrylamide, iodoacetamide, succinimidyl ester, succinimidyl carbonate, succinimidyl carbamates, sulfosuccinimidyl ester, sulfosuccinimidyl carbonate and combinations thereof.

20. The biocompatible, cross-linked polymer according to claim 13, wherein the electrophilic cross-linking agent contains a backbone that carries or is substituted with n≥2 electrophilic groups, said backbone being selected from the group of polymers consisting of agar, starch, pullulan, inulin, levan, silk, fibronectin, pectin, cellulose collagen, elastin, gelatine, albumin, fibrin, fibrinogen, dextran, methyl cellulose, hyaluronic acid, chondroitin sulfate, keratosulfate, heparan sulfate, dermatan sulfate, alginic acid, chitosan, chitin, heparin, polyvinyl alcohol, polyethylene glycol and combinations thereof.

21. A kit for producing a biocompatible, tissue-adhesive, cross-linked polymer according to claim 13, said kit comprising a NU-POX and an electrophilic cross-linking agent as defined in claim 13; wherein the kit comprises separately packaged volumes of the NU-POX and the electrophilic cross-linking agent, wherein each of the NU-POX and the cross-linking agent is present in the form of a fluid or reconstitutable powder.

22. The kit according to claim 21, wherein the NU-POX is present in the form of fluid comprising a solvent and 1-95 wt. % of the NU-POX.

23. A kit for producing a biocompatible, tissue-adhesive cross-linked polymer according to claim 13, said kit comprising a powder consisting of particles having a weight averaged mean diameter of 0.01-1000 μm, said particles including particles containing NU-POX as defined in claim 13 and particles containing the electrophilical cross-linking agent as defined in claim 13.

* * * * *